(12) United States Patent
Yoon et al.

(10) Patent No.: US 10,722,585 B2
(45) Date of Patent: *Jul. 28, 2020

(54) SUSTAINED-RELEASE LIPID PRE-CONCENTRATE OF GNRH ANALOGUES AND PHARMACEUTICAL COMPOSITION COMPRISING THE SAME

(71) Applicant: Chong Kun Dang Pharmaceutical Corp., Seoul (KR)

(72) Inventors: Sang Phil Yoon, Gyeonggi-do (KR); Ki Seong Ko, Gyeonggi-do (KR); Ha Na Yu, Gyeonggi-do (KR); Hye Jung Baik, Gyeonggi-do (KR); Won Kyu Yang, Gyeonggi-do (KR); Jin Young Ko, Gyeonggi-do (KR); So Hyun Park, Gyeonggi-do (KR); Sung Bum Jung, Gyeonggi-do (KR); Sung Won An, Gyeonggi-do (KR); Min Hyo Ki, Gyeonggi-do (KR)

(73) Assignee: Chong Kun Dang Pharmaceutical Corp., Seoul (KR)

(*) Notice: Subject to any disclaimer, the term of this patent is extended or adjusted under 35 U.S.C. 154(b) by 369 days.

This patent is subject to a terminal disclaimer.

(21) Appl. No.: 14/440,060

(22) PCT Filed: Dec. 27, 2013

(86) PCT No.: PCT/KR2013/012269
§ 371 (c)(1),
(2) Date: Apr. 30, 2015

(87) PCT Pub. No.: WO2014/104791
PCT Pub. Date: Jul. 3, 2014

(65) Prior Publication Data
US 2015/0297726 A1    Oct. 22, 2015

(30) Foreign Application Priority Data

Dec. 28, 2012  (KR) .................. 10-2012-0157583

(51) Int. Cl.
| | | |
|---|---|---|
| *A61K 47/26* | (2006.01) | |
| *A61K 9/00* | (2006.01) | |
| *A61K 38/09* | (2006.01) | |
| *A61K 47/24* | (2006.01) | |
| *A61K 47/22* | (2006.01) | |
| *A61K 47/28* | (2006.01) | |
| *A61K 9/107* | (2006.01) | |

(52) U.S. Cl.
CPC ............ *A61K 47/26* (2013.01); *A61K 9/0019* (2013.01); *A61K 9/1075* (2013.01); *A61K 38/09* (2013.01); *A61K 47/22* (2013.01); *A61K 47/24* (2013.01); *A61K 47/28* (2013.01)

(58) Field of Classification Search
None
See application file for complete search history.

(56) References Cited

U.S. PATENT DOCUMENTS

| | | | |
|---|---|---|---|
| 4,816,553 A | 3/1989 | Baur | 528/245 |
| 5,211,952 A * | 5/1993 | Spicer | A61K 38/09 128/830 |
| 5,480,656 A | 1/1996 | Okada et al. | 424/493 |
| 5,658,575 A | 8/1997 | Ribier et al. | 424/401 |
| 5,807,573 A | 9/1998 | Ljusberg-Wahren et al. | 424/450 |
| 5,888,533 A | 3/1999 | Dunn | 424/423 |
| 5,939,096 A | 8/1999 | Clerc et al. | 424/450 |
| 5,968,895 A * | 10/1999 | Gefter | A61K 38/09 514/10.1 |
| 6,328,979 B1 | 12/2001 | Yamashita et al. | 424/400 |
| 6,482,517 B1 | 11/2002 | Anderson | 428/402.24 |
| 6,552,002 B2 | 4/2003 | Steber et al. | 514/30 |
| 6,773,714 B2 | 8/2004 | Dunn et al. | 424/426 |
| 7,026,290 B1 * | 4/2006 | Domb | A61K 9/1075 424/451 |
| 7,374,779 B2 | 5/2008 | Chen et al. | 424/451 |

(Continued)

FOREIGN PATENT DOCUMENTS

| | | |
|---|---|---|
| CA | 2845784 | 3/2013 |
| CN | 101123949 A | 2/2008 |

(Continued)

OTHER PUBLICATIONS

Persad et al (Int J Clin Pract, 2002, 56(5), 389-96). (Year: 2002).*
Letter/Written Disclosure of the Supplemental Information Disclosure Statement for the above-referenced application, filed herewith on Jun. 9, 2017, 2 pages.
Response, dated Apr. 19, 2017, to Examiner's Report, dated Oct. 19, 2016, in connection with related Canadian Patent Application No. 2,888,711, 12 pages.
Request for Continued Examination and Preliminary Amendment, dated May 1, 2017, responsive to the Final Office Action, dated Nov. 29, 2016, in connection with related U.S. Appl. No. 14/440,059, 51 pages.
Response, dated May 24, 2017, to Final Office Action, dated Mar. 28, 2017, in connection with related U.S. Appl. No. 14/440,058, 13 pages.
Letter/Written Disclosure of the Supplemental Information Disclosure Statement for the above-referenced application, filed herewith on Dec. 8, 2016, 2 pages.

(Continued)

*Primary Examiner* — Celeste A Roney
(74) *Attorney, Agent, or Firm* — Dentons US LLP; Stephanie Seidman

(57) ABSTRACT

Disclosed is a pharmaceutical composition, comprising: a) at least one sorbitan unsaturated fatty acid ester having a polar head with at least two or more —OH (hydroxyl) groups; b) at least one phospholipid; c) at least one liquid crystal hardener which is free of an ionizable group and has a triacyl group with 15 to 40 carbon atoms or a carbon ring structure in a hydrophobic moiety; and d) at least one GnRH (gonadotropin-releasing hormone) analogue as a pharmacologically active substance, wherein said lipid pre-concentrate exists as a liquid phase in absence of aqueous fluid and forms into a liquid crystal in presence of aqueous fluid. The pharmaceutical composition is configured to enhance the sustained release of the pharmacologically active substance GnRH analogue.

24 Claims, 2 Drawing Sheets

(56) References Cited

U.S. PATENT DOCUMENTS

| | | | |
|---|---|---|---|
| 7,662,408 B2 | 2/2010 | Saito et al. | 424/468 |
| 7,731,947 B2 | 6/2010 | Eliaz et al. | 424/85.4 |
| 7,871,642 B2 | 1/2011 | Supersaxo et al. | 424/450 |
| 8,236,292 B2 * | 8/2012 | Thuresson | A61K 8/0295 424/85.7 |
| 9,173,853 B2 | 11/2015 | Lee et al. | 424/489 |
| 2003/0070679 A1 | 4/2003 | Hochrainer et al. | 128/203.15 |
| 2005/0077497 A1 * | 4/2005 | Anderson | A61K 9/1274 252/299.1 |
| 2005/0118206 A1 | 6/2005 | Luk et al. | 424/400 |
| 2006/0165766 A1 | 7/2006 | Barenholz et al. | 424/450 |
| 2006/0182790 A1 | 8/2006 | Mayoral | 424/448 |
| 2007/0080323 A1 | 4/2007 | Joabsson et al. | 252/299.01 |
| 2008/0085263 A1 | 4/2008 | Thuresson et al. | 424/85.7 |
| 2008/0102128 A1 | 5/2008 | Constancis et al. | 424/489 |
| 2008/0139392 A1 | 6/2008 | Acosta-Zara et al. | 504/359 |
| 2008/0274176 A1 | 11/2008 | Johnsson et al. | 424/463 |
| 2010/0034801 A1 | 2/2010 | Li et al. | 424/94.61 |
| 2010/0125060 A1 | 5/2010 | Razzak et al. | 514/210.05 |
| 2011/0091420 A1 | 4/2011 | Liu et al. | 424/85.4 |
| 2012/0269772 A1 | 10/2012 | Thuresson et al. | 424/85.7 |
| 2014/0206616 A1 | 7/2014 | Ko et al. | 514/11.7 |
| 2015/0110876 A1 | 4/2015 | Lee et al. | 424/489 |
| 2015/0265535 A1 | 9/2015 | Yu et al. | 424/400 |
| 2015/0290322 A1 | 10/2015 | Yoon et al. | 514/64 |
| 2015/0322023 A1 | 11/2015 | Lee et al. | 546/290 |
| 2015/0374850 A1 | 12/2015 | Hwang et al. | 424/489 |

FOREIGN PATENT DOCUMENTS

| | | | |
|---|---|---|---|
| CN | 103764127 A | | 4/2014 |
| EP | 0 224 987 | | 6/1987 |
| EP | 0760237 | | 3/1997 |
| JP | 62-129226 | | 6/1987 |
| JP | H08-506584 | | 7/1996 |
| JP | 2003-520205 | | 7/2003 |
| JP | 2007-510705 | | 4/2007 |
| JP | 2007-511525 | | 5/2007 |
| JP | 2008-526934 | | 7/2008 |
| KR | 10-2012-0157583 | | 12/2012 |
| KR | 10-2012-0093677 | | 3/2013 |
| NZ | 280420 | | 3/1997 |
| NZ | 280419 | | 4/1997 |
| WO | WO 1994/017830 | | 8/1994 |
| WO | WO 98/47487 | | 10/1998 |
| WO | WO 1999/033491 | | 7/1999 |
| WO | WO 2001/034111 | | 5/2001 |
| WO | WO 2005/046642 | | 5/2005 |
| WO | WO 2005/048930 | | 6/2005 |
| WO | WO 2005/048952 | | 6/2005 |
| WO | WO 2005/074896 | | 8/2005 |
| WO | WO 2005/117830 | | 12/2005 |
| WO | WO 2006/075124 | | 7/2006 |
| WO | WO 2006/075125 | | 7/2006 |
| WO | WO 2006/077362 | | 7/2006 |
| WO | WO 2006/108556 | | 10/2006 |
| WO | WO 2008/152401 | | 12/2008 |
| WO | WO 2009/024795 | | 2/2009 |
| WO | WO 2009/024797 | | 2/2009 |
| WO | WO 2011/112875 | | 9/2011 |
| WO | WO 2012/128417 | | 9/2012 |
| WO | WO 2013/032207 | | 3/2013 |
| WO | WO-2013032207 A1 * | 3/2013 | A61K 9/0019 |
| WO | WO 2014/104784 | | 7/2014 |

OTHER PUBLICATIONS

English language abstract of CN 101978947 A, accessed from Espacenet on Sep. 9, 2016, 1 page.
English language translation of Korean Patent Application No. 10-2012-0157583 and verification, submitted Jan. 28, 2014, 50 pages.
Hammond et al, "Soybean Oil, Bailey's industrial oil and fat products," Sixth Ed., Six Volume Set., Edited by Fereidoon Shahidi, John Wiley & Sons, Inc., p. 579, Table 3 (2005).
Kato, et al., "Temperature-sensitive nonionic vesicles prepared from Span 80 (Sorbitan Monooleate)," Langmuir 24(19):10762-10770 (2008).
Lindell et al., "Influence of a charged phospholipid on the release pattern of timolol maleate from cubic liquid crystalline phases," Progr. Colloid. Polym. Sci. 108: 111-118 (1998).
Lynch et al., "Enhanced loading of water-soluble actives into biocontinuous cubic phase liquid crystals using cationic surfactants," Journal of Colloid and Interface Science 260:404-413 (2003).
Machine-generated English language translation of JP 2003-252748, published Sep. 10, 2003, 5 pages.
Shah et al., "The ionic structure of lecithin monolayers," Journal of Lipid Research. 8:227-233 (1967).
V.Y. Chueshov, "Industrial technology of drugs," vol. 1. NFAU, p. 24, paragraphs 2.2. and 2.2.1. [English translation and original document in Russian], 3 pages, (2002).
Yeap et al., "Effect of calcium ions on the density of lecithin and its effective molecular volume in lecithin-water dispersions," Chemistry and Physics of Lipids. 151(1): 1-9 (2008).
Yuan et al., "Linker-based lecithin microemulsions for transdermal delivery of lidocaine," International Journal of Pharmaceutics 349:130-143 (2008).
Examiner's Report, dated Dec. 17, 2015, in connection with related Canadian Patent Application No. 2,888,711, 3 pages.
Examination Report, dated Dec. 17, 2015, in connection with corresponding Canadian Patent Application No. 2,888,863, 3 pages.
Examination Report, dated Dec. 22, 2015, in connection with related Canadian Patent Application No. 2,888,801, 3 pages.
Examination Report, dated Jan. 13, 2016, in connection with related Australian Patent Application No. 2013371094, 3 pages.
Office Action, dated Feb. 15, 2016, in connection with related Russian Patent Application No. 2014112189/15(019137) [English translation and original document in Russian], 8 pages.
Response, dated Jun. 16, 2016, to Examination Report, dated Dec. 17, 2015, in connection with corresponding Canadian Patent Application No. 2,888,863, 21 pages.
Response, dated Jun. 17, 2016, to Examiner's Report, dated Dec. 17, 2015, in connection with related Canadian Patent Application No. 2,888,711, 14 pages.
Response, dated Jun. 17, 2016, to Examination Report, dated Dec. 22, 2015, in connection with related Canadian Patent Application No. 2,888,801, 21 pages.
Extended European Search Report, dated Jul. 12, 2016, in connection with related European Patent Application No. 13866593.0, 9 pages.
Extended European Search Report, dated Jul. 19, 2016, in connection with corresponding European Patent Application No. 13867921.2, 9 pages.
Office Action, dated Jul. 29, 2016, in connection with related Russian Patent Application No. 2015131109 [English translation and original document in Russian], 16 pages.
Response, filed Aug. 2, 2016, to Office Action, dated Feb. 4, 2016, in connection with related U.S. Appl. No. 14/241,696, 10 pages.
Office Action, dated Aug. 8, 2016, in connection with related U.S. Appl. No. 14/440,058, 10 pages.
Office Action, dated Aug. 25, 2016, issued in connection with related Russian Patent Application No. 2015131112 [English translation and original document in Russian], 14 pages.
Notice of Allowance, dated Sep. 12, 2016, in connection with related U.S. Appl. No. 14/241,696, 21 pages.
Examiner's Requisition, dated Sep. 28, 2016, in connection with related Canadian Patent Application No. 2,888,801, 4 pages.
Examination Report, dated Sep. 29, 2016, in connection with corresponding Canadian Patent Application No. 2,888,863, 4 pages.
Response, dated Oct. 17, 2016, to Office Action, dated Jul. 5, 2016, in connection with related U.S. Appl. No. 14/440,059, 48 pages.
Examiner's Report, dated Oct. 19, 2016, in connection with related Canadian Patent Application No. 2,888,711, 4 pages.
Response, dated Oct. 21, 2016, to Examination Report, dated Jan. 13, 2016, in connection with related Australian Patent Application No. 2013371094, 18 pages.

(56) References Cited

OTHER PUBLICATIONS

Response, dated Oct. 24, 2016, to Examination Report, dated Jan. 13, 2016, in connection with related Australian Patent Application No. 2013371098, 25 pages.
Notice of Acceptance, dated Nov. 7, 2016, in connection with related Australian Patent Application No. 2013371094, 3 pages.
Notice of Acceptance, dated Nov. 7, 2016, in connection with related Australian Patent Application No. 2013371098, 3 pages.
Final Office Action, dated Nov. 29, 2016, in connection with related U.S. Appl. No. 14/440,059, 46 pages.
Response, filed Nov. 30, 2016, to Office Action, dated Aug. 8, 2016, in connection with related U.S. Appl. No. 14/440,058, 32 pages.
Response, dated Nov. 30, 2016, to Examination Report, dated Jan. 13, 2016, in connection with corresponding Australian Patent Application No. 2013371101, 26 pages.
U.S. Appl. No. 14/241,696, filed Feb. 27, 2014, 2014/0206616, Jul. 24, 2014.
U.S. Appl. No. 14/440,058, filed Apr. 30, 2015.
U.S. Appl. No. 14/440,059, filed Apr. 30, 2015.
Letter/Written Disclosure of the Supplemental Information Disclosure Statement for the above-referenced application, filed herewith on Jul. 14, 2016, 2 pages.
English language translation of title and abstract of WO 2012/128417, published Sep. 27, 2012, 1 page.
Machine-generated English translation of WO 2012/128417, published Sep. 27, 2012, PatentScope, World Intellectual Property Organization, 6 pages.
Machine-generated English translation of WO 2012/165468, published Dec. 6, 2012, PatentScope, World Intellectual Property Organization, 16 pages.
Nema et al., "Excipients and their use in injectable products," PDA J Pharm Sci Technol 51(4):166-171 (1997).
Scholfield, C.R., "Composition of Soybean Lecithin." J. American Oil Chemist's Society 58(10):889-892 (1981).
International Search Report and Written Opinion, dated Dec. 12, 2012, in conncection with International Patent Application No. PCT/KR2012/006855, 12 pages.
International Preliminary Report on Patentability, dated Mar. 4, 2014, in connection with International Patent Application No. PCT/KR2012/006855, 6 pages.
Office Action, dated Feb. 10, 2015, in connection with U.S. Appl. No. 14/241,696, 15 pages.
Amendment and Response, dated Aug. 4, 2015, in connection with U.S. Appl. No. 14/241,696, 31 pages.
Final Office Action, dated Oct. 15, 2015, in connection with U.S. Appl. No. 14/241,696, 14 pages.
Request for Continued Examination and Preliminary Amendment, dated Jan. 15, 2016, in connection with U.S. Appl. No. 14/241,696, 12 pages.
Office Action, dated Feb. 4, 2016, in connectionwith U.S. Appl. No. 14/241,696, 20 pages.
Examination Report, dated Mar. 24, 2015, in connection with Australian Patent Application No. 2012302422, 3 pages.
Response, submitted Sep. 18, 2015, in connection with Australian Patent Application No. 2012302422, 18 pages.
Notice of Acceptance, dated Sep. 25, 2015, in connection with Australian Patent Application No. 2012302422, 2 pages.
Examiner's Report, dated Feb. 12, 2015, in connection with Canadian Patent Application No. 2,845,784, 3 pages.
Response, dated Jul. 28, 2015, to Examiner's Report in connection with Canadian Patent Application No. 2,845,784, 13 pages.
Examiner's Report, dated Nov. 12, 2015, in connection with Canadian Patent Application No. 2,845,784, 4 pages.
Supplementary European Search Report and Written Opinion, dated May 8, 2015, in connection with European Patent Application No. EP 12 826 818.2, 3 pages.
Response to Supplementary European Search Report and Written Opinion, dated Nov. 18, 2015, in connection with European Patent Application No. EP 12 826 818.2, 16 pages.

Official Action, dated Jul. 28, 2015, in connection with Japanese Patent Application No. 2014-528270, [Original document in Japanese and English translation], 5 pages.
Office Action, dated Nov. 28, 2014, in connection with New Zealand Patent Application No. 622165, 2 pages.
Office Action, dated Jul. 5, 2016, in connection with U.S. Appl. No. 14/440,059, 34 pages.
Examination Report, dated Jan. 13, 2016, in connection with Australian Patent No. 2013371098, 3 pages.
Extended European Search Report, dated May 17, 2016, in connection with European Patent Application No. 13868908.8, 7 pages.
Office Action, dated May 31, 2016, in connection with Japanese Patent Application No. 550322/2015 [English language translation and original document in Japanese], 9 pages.
Examination Report, dated Sep. 23, 2015, in connection with New Zealand Patent Application No. 710471, 3 pages.
Response, filed Mar. 22, 2016, to Examination Report, dated Sep. 23, 2015, in connection with New Zealand Patent Application No. 710471, 11 pages.
Notification of Acceptance, dated Apr. 18, 2016, in connection with New Zealand Patent Application No. 710471, 1 page.
Examination Report, dated Jan. 13, 2016, in connection with Australian Patent Application No. 2013371101, 3 pages.
Office Action, dated Jun. 7, 2016, in connection with Japanese Patent Application No. 550323/2015 [English language translation and original document in Japanese], 14 pages.
Letter/Written Disclosure of the Supplemental Information Disclosure Statement for the above-referenced application, filed herewith on Mar. 15, 2017, 2 pages.
Amar-Yuli et al., "Solubilization of Food Bioactives with Lyotropic Liquid Crystalline Mesophases," Current Opinion in Colloid & Interface Science 14:21-32 (2009).
Response, filed Mar. 10, 2016, to Examiner's Report, dated Nov. 12, 2015, in connection with related Canadian Patent Application No. 2,845,784, 16 pages.
Examiner's Report, dated May 4, 2016, in connection with related Canadian Patent Application No. 2,845,784, 4 pages.
Response, filed May 19, 2016, to Examiner's Report, dated May 4, 2016, in connection with related Canadian Patent Application No. 2,845,784, 6 pages.
Response, filed Dec. 13, 2016, to Extended European Search Report, dated May 17, 2016, in connection with related European Patent Application No. 13868908.8, 12 pages.
Notice of Acceptance, dated Dec. 20, 2016, in connection with corresponding Australian Patent Application No. 2013371101, 3 pages.
Response, filed Jan. 26, 2017, to Extended Euorpean Search Report, dated Jul. 12, 2016, in connection with related European Patent Application No. 13866593.0, 15 pages.
Office Action, dated Jan. 17, 2017, in connection with related Chinese Patent Application No. 201380068015.5 [English translation and original document in Chinese], 14 pages.
Official Action, dated Jan. 27, 2017, in connection with corresponding Russian Patent Application No. 2015131107 [English language translation and original document in Russian], 10 pages.
Response, dated Feb. 14, 2017, to Extended European Search Report, dated Jul. 19, 2016, in connection with corresponding European Patent Application No. 13867921.2, 19 pages.
Letter/Written Disclosure of the Supplemental Information Disclosure Statement for the above-referenced application, filed herewith on May 4, 2017, 2 pages.
Office Action, dated Mar. 24, 2017, in connection with corresponding Chinese Patent Application No. 201380067822.5, [English translation and original document in Chinese], 21 pages.
Response, dated Mar. 27, 2017, to Examination Report, dated Sep. 28, 2016, in connection with related Canadian Patent Application No. 2,888,801, 11 pages.
Final Office Action, dated Mar. 28, 2017, in connection with related U.S. Appl. No. 14/440,058, 11 pages.
Response, dated Mar. 29, 2017, to Examination Report, dated Sep. 29, 2016, in connection with corresponding Canadian Patent Application No. 2,888,863, 11 pages.

(56) References Cited

OTHER PUBLICATIONS

Letter/Written Disclosure of the Information Disclosure Statement for the above-referenced application, dated Jul. 31, 2015, 2 pages.
Athanasiou et al., "Sterilization, Toxicity, Biocompatibility, and Clinical Applications of Polylactic Acid/Polyglycolic Acid Copolymers." Biomaterials 17(2):93-102 (1996).
Ljusberg-Wahren et al., "Enzymatic characterization of lipid-bsaed drug delivery systems. " Int. J. Pharm 298(2):328-332 (2005).
Sah, H. and Bahl, Y. "Effects of acieous phase composition upon protein destabilization at water/organic solvent interface," J. Control Release 106(1-2):51-61 (2005).
International Search Report and Written Opinion, dated Apr. 28, 2014, in connection with International Patent Application No. PCT/KR2013/012269, 11 pages.
International Preliminary Report on Patentability, dated Jun. 30, 2015, in connection with International Patent Application No. PCT/KR2013/012269, 7 pages.
Letter/Written Disclosure of the Supplemental Information Disclosure Statement for the above-referenced application, dated Aug. 24, 2015, 2 pages.
International Search Report and Written Opinion, dated Apr. 9, 2014, in connection with International Patent Application No. PCT/KR2013/012265, 12 pages.
International Search Report and Written Opinion, dated Apr. 28, 2014, in connection with International Patent Application No. PCT/KR2013/012259, 12 pages.
International Preliminary Report on Patentability, dated Jun. 30, 2015, in connection with International Patent Application No. PCT/KR2013/012259, 8 pages.
International Preliminary Report on Patentability, dated Jun. 30, 2015, in connection with International Patent Application No. PCT/KR2013/012265, 8 pages.
Letter/Written Disclosure of the Supplemental Information Disclosure Statement for the above-referenced application, filed herewith on Feb. 22, 2018, 3 pages.
Office Action, dated Dec. 18, 2017, in connection with corresponding Chinese Patent Application No. 201380067822.5 [English translation and original document in Chinese], 27 pages.
Decision to Grant, dated Jan. 25, 2018, in connection with corresponding European Patent Application No. 13867921.2, 2 pages.
Letter/Written Disclosure of the Supplemental Information Disclosure Statement for the above-referenced application, filed herewith on Feb. 28, 2018, 2 pages.
Certificate of Grant, dated Mar. 2, 2017, in connection with Australian Patent Application No. 2013371094, 1 page.
Request for Continued Examination, filed Jul. 26, 2017, in connection with U.S. Appl. No. 14/440,058, 3 pages.
Office Action, dated Nov. 14, 2017, in connection with U.S. Appl. No. 14/440,058, 7 pages.
Office Action, dated Nov. 1, 2017, in connection with U.S. Appl. No. 14/440,059, 36 pages.
Communication Pursuant to Article 94(3) EPC (Examination Report), dated Nov. 27, 2017, in connection with European Patent Application No. 13 868 908.8, 6 pages.
Communication Pursuant to Article 94(3) EPC (Examination Report), dated Jan. 9, 2018, in connection with European Patent Application No. 13 866 593.0 [D1 = WO 2005/046642; D2 = US 2008/102128; D3 = US 2010/125060; D4 = US 2008/139392; D5 = Yuan et al., International Journal of Pharmaceutics 349:130-143 (2008)], 4 pages.
Response, filed Feb. 13, 2018, to Office Action, dated Nov. 14, 2017, in connection with U.S. Appl. No. 14/440,058, 22 pages.
Letter/Written Disclosure of the Supplemental Information Disclosure Statement for the above-referenced application, filed herewith on Jan. 11, 2019, 2 pages.
Response, filed Mar. 29, 2018, to Office Action, dated Nov. 1, 2017, in connection with U.S. Appl. No. 14/440,059, 46 pages.
Final Office Action, dated Apr. 18, 2018, in connection with U.S. Appl. No. 14/440,059, 29 pages.
Response, filed Mar. 27, 2018, to Communication Pursuant to Article 94(3) EPC (Examination Report), dated Nov. 27, 2017, in connection with European Patent Application No. 13 868 908.8, 2 pages.
Response, filed May 17, 2018, to Communication Pursuant to Article 94(3) EPC (Examination Report), dated Jan. 9, 2018, in connection with European Patent Application No. 13 866 593.0, 15 pages.
Letter/Written Disclosure of the Supplemental Information Disclosure Statement for the above-referenced application, filed herewith on Oct. 1, 2019, 2 pages.
Gustafsson et al., "Submicron Particles of Reversed Lipid Phases in Water Stabilized by a Nonionic Amphiphilic Polymer," Langmuir 13:6964-6971 (1997).
Response, filed Nov. 7, 2016, to Office Action, dated Jun. 7, 2016, in connection with Japanese Patent Application No. 2015-550323 [machine-generated English translation and document in Japanese, as accessed from <URL:j-platpat.inpit.go.jp/ on May 30, 2019], 51 pages.
Decision to Grant, dated Dec. 15, 2016, in connection with Japanese Patent Application No. 2015-550323 [machine-generated English translation and document in Japanese, as accessed from <URL:j-platpat.inpit.go.jp/ on May 30, 2019], 7 pages.

* cited by examiner

[Fig. 1]
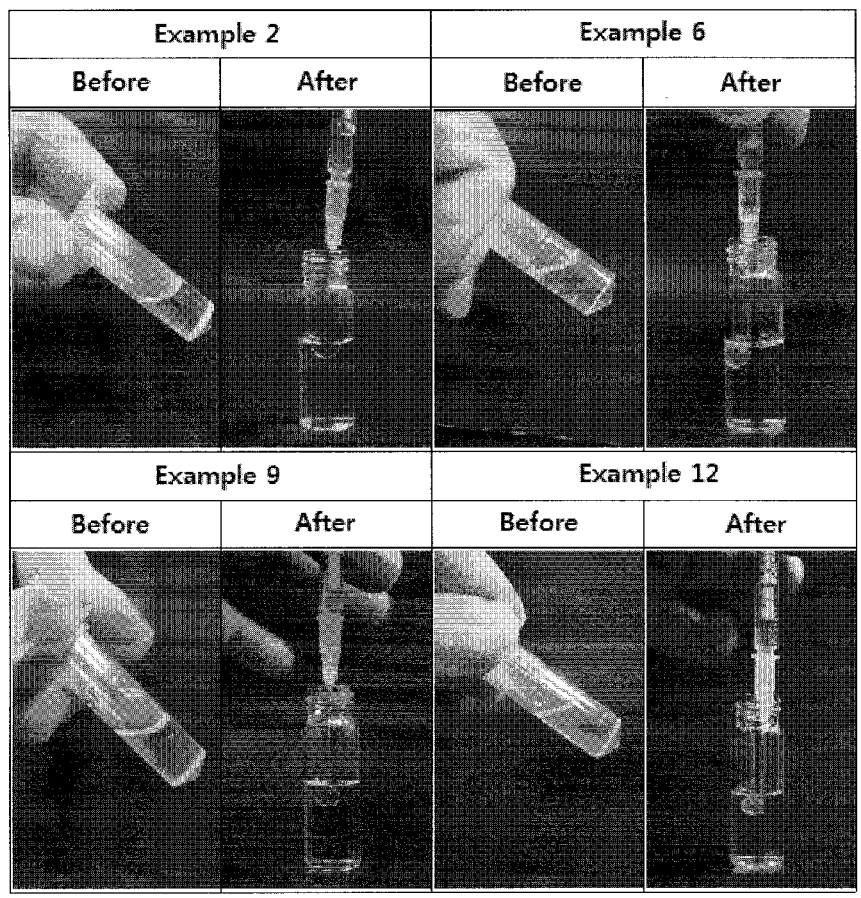
[Fig. 2]
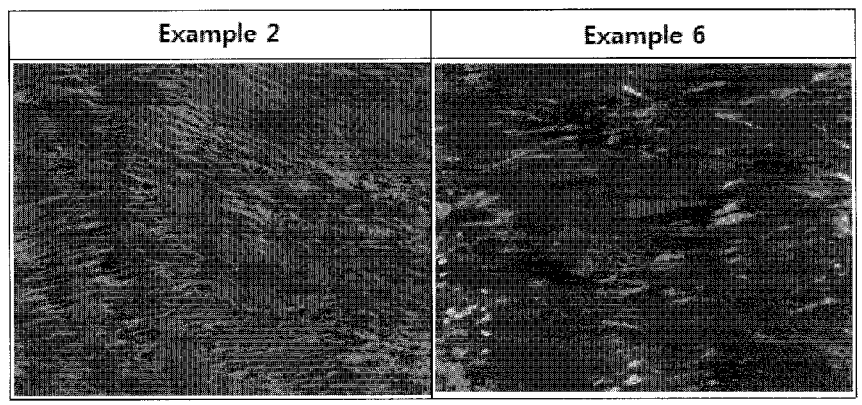

[Fig. 3]
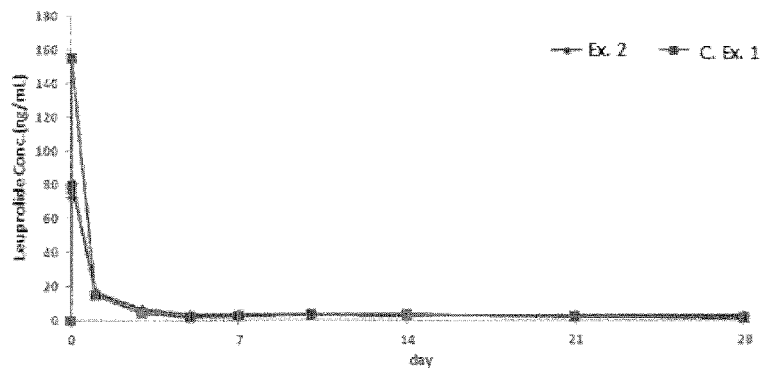
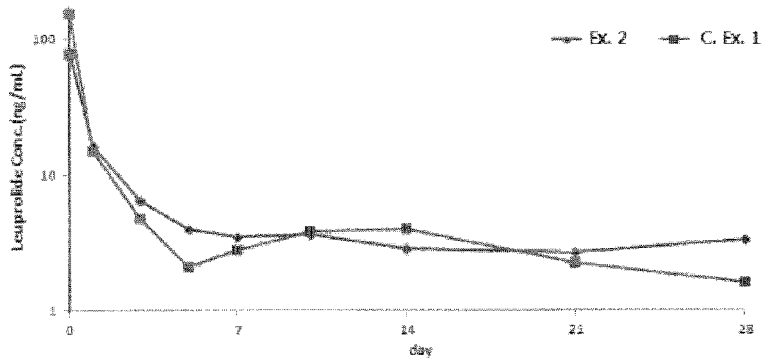
[Fig. 4]
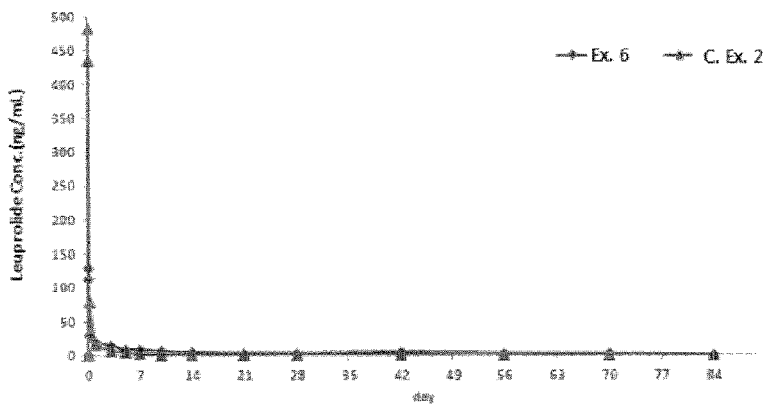
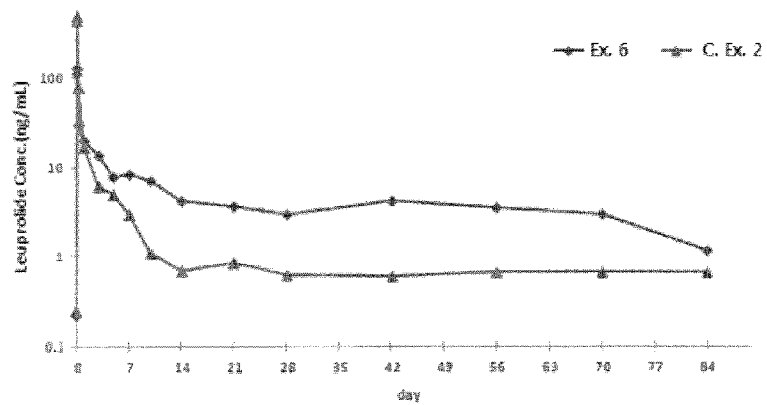

SUSTAINED-RELEASE LIPID PRE-CONCENTRATE OF GNRH ANALOGUES AND PHARMACEUTICAL COMPOSITION COMPRISING THE SAME

RELATED APPLICATIONS

This application is the U.S. National Stage of International Application. No. PCT/KR2013/012269, filed 27 Dec. 2013, which claims benefit of priority to Korean Patent Application KR-10-2012-0157583, filed 28 Dec. 2012, the specification of which is incorporated by reference herein.

TECHNICAL FIELD

The present invention relates to a sustained-release lipid pre-concentrate comprising a GnRH analogue as a pharmacologically active substance, and a pharmaceutical composition comprising the same.

BACKGROUND ART

Sustained release formulations are designed to release a single dose of a pharmacologically active substance at a predetermined rate in order to maintain the effective concentration of the substance in the blood stream for a specific period of time, with minimization of the side effects caused by multiple doses.

In consideration of the therapeutic mechanism and physical and chemical properties thereof, gonadotropin-releasing hormone (GnRH) derivatives are representative of pharmacologically active substance to be designed as sustained-release formulations.

Gonadotropin-releasing hormone (GnRH) or luteinizing hormone-releasing hormone (LHRH) is a neuroendocrine peptide which is synthesized and released from neurons in the neurovascular terminal of hypothalamus. Once being released from the hypothalamus, GnRH selectively binds to specific receptors on the membrane of anterior pituitary gonadotroph cells to induce the biosynthesis and release of follicle-stimulating hormone (FSH) and leuteinizing hormone (LH). FSH and LH act to regulate the production of sex steroids from sex glands in males and females. Due to the biological functions of GnRH, its analogues may be useful for the treatment of sex hormone-dependent diseases such as prostate cancer, breast cancer, ovarian cancer, endometriosis, uterine fibroid, polycystic ovary syndrome, hypertrichosis, precocious puberty, gonadotroph pituitary adenomas, sleep apnea syndrome, irritable bowel syndrome, premenstrual syndrome, benign prostatic hyperplasia, and infertility.

Lupron® Depot is a commercially available, intramuscular or subcutaneous injection for the sustained release of the GnRH analogue leuprolide acetate, with the biodegradable PLGA [poly(lactic-co-glycolic acid)] microparticles delivering as a sustained release matrix. Generally, PLGA microparticles degrade into lactic acid and glycolic acid over a specific period of time in vivo, releasing the pharmacologically active substance loaded there within in a sustained manner (U.S. Pat. No. 5,480,656). However, not only are the fabrication processes of PLGA microparticles complicated and difficult, but also pharmacologically active substances are loaded thereinto with significantly poor efficiency. In addition, because a PLGA microparticles are difficult to filter sterilization, and melt at 40° C. or higher, the sterilization thereof cannot be achieved with general processes, but requires highly sterile conditions. An ideal sustained-release profile is obtained using two or more different PLGA microparticles which, however, further complicate the processes of fabrication and mixing (WO 2005/074896), increasing the production cost. In addition, acetic acid impurities and acidic degradation products from PLGA microparticles induce inflammation and reduce cell growth rates (K. Athanasiou, G. G. Niederauer, and C. M. Agrawal, Biomaterials, 17, 93 (1996)). For the sustained release, a suspension of 10~100 μm PLGA microparticles in an aqueous solution is injected in a significant amount, but this gives rise to a pain or a tissue damage at the injection site.

Eligard® was introduced as a sustained-release injection formulation for a GnRH analogue (leuprolide acetate) which compensates the problems with PLGA microparticle-based sustained-release formulations. Eligard® is widely marketed as a subcutaneous injection which is prepared by dissolving PLGA [poly(DL-lactide-co-glycolide)] having a protected carboxyl terminal group and a GnRH analogue (leuprolide acetate) in N-methyl-2-pyrrolidone (NMP). Eligard® exists as a flowable composition which can be prepared by dissolving a biodegradable polymer in a polar aprotic solvent, and is designed as a subcutaneous injection with an improvement in partially drawbacks with solid PLGA microparticle formulations (U.S. Pat. No. 6,773,714). This commercial product is very poor in usability because of no supply of a complete prefilled syringes device, and exhibits low drug stability upon the mixture solution. The device provided in the product comprises two syringes which can be connected to each other, and mixing, preparing and injecting tools. A final mixture solution is not obtained until more than about 10 steps are carried out, and only 30 mins is given to an entire process from preparation to injection. In addition, the product must be stored in a refrigerator, and unless stored in a refrigerator, the final mixed solution cannot be used for more than 5 days. Moreover, no improvements are observed in the product with regard to a high initial burst, which is a drawback typical to PLGA microparticle formulations. Rather, the product exhibits higher initial burst concentration, compared to the PLGA microparticle formulation Lupron® Depot (U.S. Pat. No. 6,773,714). An initial burst concentration greatly exceeding that at which a drug can function is undesirable in both functionally and toxicologically. Particularly in consideration of the mechanism of the GnRH analogue in which the sex hormone release is temporally increased at an initial stage of administration, and then down-regulated from a certain time point, an excessive initial burst concentration must be avoided. International Patent Publication No. WO 2005/117830 describes a pre-formulation comprising at least one neutral diacyl lipid and/or at least one tocopherol, at least one phospholipid, and at least one biocompatible, oxygen containing, low viscosity organic solvent. Another alternative is described in the International Patent Publication No. WO 2006/075124 which concerns a pre-formation comprising at least one diacyl glycerol, at least one phosphatidyl choline, at least one oxygen containing organic solution, and at least one GnRH analogue. These pre-formulations allow the sustained release of a pharmacologically active substance in vivo for four weeks, and do not form lactic acid or glycolic acid degradation products from their polymer systems, thus not causing pain or inflammation. However, there is a problem with the formulations in that the use of a diacyl lipid, a component essential for the pre-formulations, as a pharmaceutical excipient is not usable and it has to be proven to be sufficiently safe, and that their obligatory organic solvent incurs a reduction in the activity of some pharmacologically active substances (H. Ljusberg-Wahre, F.

S. Nielse, 298, 328-332 (2005); H. Sah, Y. Bahl, Journal of Controlled Release 106, 51-61(2005)).

Culminating in the present inventors suggested a sustained-release lipid pre-concentrate comprising a) sorbitan unsaturated fatty acid ester; b) a phospholipid; and c) a liquid crystal hardener, and a pharmaceutical composition comprising the pre-concentrate (Korean Patent Application No. 10-2012-0093677). This sustained-release lipid pre-concentrate exhibits in vivo safety and biodegradability at the same or higher levels, compared to conventional pre-concentrates and the pharmaceutical composition is found to allow for the sustained release of the pharmacologically active substance loaded therein.

Moreover, the further research of the present inventors resulted in the finding that when applied to the sustained-release lipid pre-concentrate, a GnRH analogue can be released in a sustained manner at a concentration sufficient to act as a pharmacological active substance in vivo, leading to the present invention.

A description is given of the prior arts relevant to the present invention, infra.

U.S. Pat. No. 7,731,947 describes a composition comprising: a particle formulation comprising an interferon, sucrose, methionine, and a citrate buffer, and a suspending solution comprising a solvent such as benzyl benzoate, wherein the particle formulation is dispersed in the suspending solution, elucidating the application of GnRH analogues thereto. In one Example, it is described that phosphatidylcholine is dissolved together with vitamin E (tocopherol) in an organic solvent and is used to disperse the particle formulation therein. However, this composition is different from the present invention in that the composition is used to disperse solid particles and does not allow the formation of liquid crystals.

U.S. Pat. No. 7,871,642 describes a method of preparing a dispersion for delivering a pharmacologically active substance comprising hormone formulation, dispersing a homogeneous mixture of a phospholipid, a polyoxyethylene-containing coemulsifier, triglyceride and ethanol in water, wherein the polyoxyethylene-containing surfactant is selected from among polyoxyethylene sorbitan fatty acid esters (polysorbate) and polyethoxylated vitamin E derivatives. polyoxyethylene sorbitan fatty acid esters and polyethoxylated vitamin E derivatives, derived by conjugating the hydrophilic polymer polyoxyethylene to sorbitan fatty acid ester and vitamin E, respectively, are quite different in structure from sorbitan fatty acid ester and vitamin E. They are usually used as hydrophilic surfactants utilizing the property of polyoxyethylene, which is different from the component of the present invention.

U.S. Pat. No. 5,888,533 describes a flowable composition for forming a solid biodegradable implant in situ within a body, comprising: a non-polymeric, water-insoluble, biodegradable material; and a biocompatible, organic solvent that at least partially solubilizes the non-polymeric, water-insoluble, biodegradable material and is miscible or dispersible in water or body fluids, and capable of diffusing-out or leaching from the composition into body fluid upon placement within a body, whereupon the non-polymeric material coagulates or precipitates to form the solid implant. In this composition, sterols, cholesteryl esters, fatty acids, fatty acid glycerides, sucrose fatty acid esters, sorbitan fatty acid esters, fatty alcohols, esters of fatty alcohols with fatty acids, anhydrides of fatty acids, phospholipids, lanolin, lanolin alcohols, and combinations thereof are described as the non-polymeric material, and ethanol is used as the solvent. However, differences from the present invention reside in that this composition cannot form liquid crystals and is designed to form solid implants by simple coagulation or precipitation of water-insoluble materials and that a lot of the organic solvent is necessarily used.

DISCLOSURE OF INVENTION

Technical Problem

It is therefore an object of the present invention to provide a pharmaceutical composition based on a sorbitan unsaturated ester having a polar head with at least two —OH (hydroxyl) groups that has significantly high safety and biodegradability and exists in a liquid state advantageous for injection applications while forming into a liquid crystal upon exposure to aqueous fluid, thus enhancing the sustained release of a GnRH analogue in vivo.

It is another object of the present invention to provide a pharmaceutical composition which can be injected without producing pain, inflammations and initial burst concentrate, problems which are reported in conventional formulations.

Solution to Problem

In accordance with an aspect thereof, the present invention provides a pharmaceutical composition, comprising a) at least one sorbitan unsaturated fatty acid ester; b) at least one phospholipid; c) at least one liquid crystal hardener; and d) at least one GnRH analogue, as a pharmacologically active substance, wherein the composition exists as a liquid phase in the absence of aqueous fluid and forms into a liquid crystal in the presence of aqueous fluid.

Below, a detailed description will be given of each component.

a) Sorbitan Unsaturated Fatty Acid Ester

For use as a liquid crystal former in the present invention, the sorbitan unsaturated fatty acid ester preferably has two or more —OH(hydroxyl) groups in the polar head. This sorbitan unsaturated fatty acid ester is represented by the following Chemical Formula 1. The compound of Chemical Formula 1 is sorbitan monoester where $R^1$=$R^2$=OH, $R^3$=R, and sorbitan diester where $R^1$=OH, $R^2$=$R^3$=R, R being an alkyl ester of 4 to 30 carbon atoms with at least one unsaturated bond.

[Chemical Formula 1]

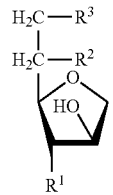

The sorbitan fatty acid ester, which accounts for the formation of a liquid crystal in the present invention, is different from conventional counterparts such as oleyl glycerate (OG), phytanyl glycerate (PG), and glycerine monooleate (GMO), glycerine dioleate (GDO) of the following Chemical Formula 2. That is, the conventional molecules responsible for liquid crystalline phases share the common structure consisting of a polar head derived from glycerine or glyceric acid and a non-polar tail derived from a lipid alcohol or fatty acid.

[Chemical Formula 2]

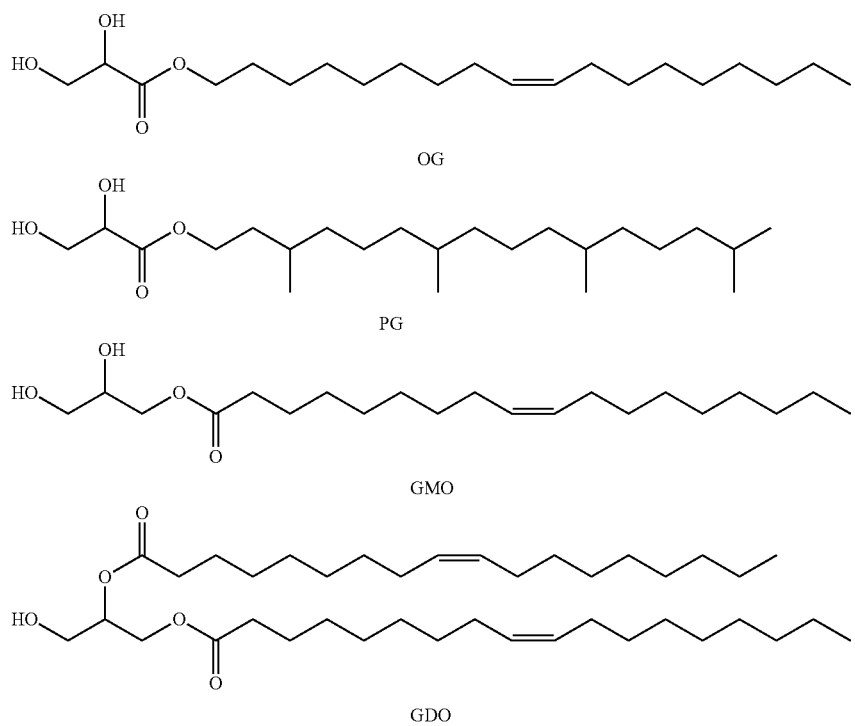

However, the conventional molecules responsible for liquid crystalline phases are somewhat difficult to apply to the development of medications because of the following disadvantages. Oleyl glycerate (OG) and phytanyl glycerate (PG), although capable of readily forming into liquid crystals, are rarely used as pharmaceutical excipients for human medicine because of their relatively high toxicity. On the other hand, glycerine monooleate (GMO) is useful as a pharmaceutically acceptable excipient, but has weak crystallinity to form liquid crystals necessary for sustained release medications.

Glycerol dioleate (GDO), which is used in International Patent Publication No. WO 2005/117830 as described supra, is a diacyl lipid with glycerin functioning as a polar head. This molecule is not generally used as a pharmaceutical excipient because its safety has not yet been proven.

Following intensive and thorough research, the present inventors found that sorbitan unsaturated fatty acid esters have advantages over conventionally used liquid crystalline molecules, glycerine or glyceric acid derivatives in that they form liquid crystals very effectively for the sustained release of pharmacologically active substance, with superiority in safety and biodegradability and are applicable to the development of medical products overcoming the problems encountered in the prior art. For use in compositions for medicaments, materials must be guaranteed to be safe and biodegradable. Further, biodegradability is a very important factor for the material which is in charge of sustained release in the body. If the sustained release injection using PLGA is designed to release a pharmacologically active substance for one week, it is ideal that the PLGA is degraded in vivo one week after injection. In fact, however, PLGA remains intact for one to several months even after the function of sustained release is finished. Therefore, the sorbitan unsaturated fatty acid ester of the present invention, which has excellent sustained release property, safety and biodegradability, is applicable for a novel liquid crystal-inducing material with great value in pharmaceutical industry.

In detail, the sorbitan unsaturated fatty acid ester of the present invention may be selected from sorbitan monoester, sorbitan sesquiester, sorbitan diester and a combination thereof, which can be derived from fatty acids obtainable from whale oils and fish oils as well as vegetable oils (e.g., coconut oil, castor oil, olive oil, peanut oil, rapeseed oil, corn oil, sesame oil, cotton seed oil, soybean oil, sunflower seed oil, safflower oil, linseed oil, etc.), and animal fats and oils (e.g., milk fat, lard, and beef tallow).

Sorbitan monoester is a compound in which one fatty acid group is attached to sorbitan via an ester bond, and may be selected from among sorbitan monooleate, sorbitan monolinoleate, sorbitan monopalmitoleate, sorbitan monomyristoleate, and a combination thereof.

Sorbitan sesquiester is a compound in which 1.5 fatty acid groups, on average, are attached to sorbitan via an ester bond, and may be selected from among sorbitan sesquioleate, sorbitan sesquilinoleate, sorbitan sesquipalmitoleate, sorbitan sesquimyristoleate, and a combination thereof.

Sorbitan diester is a compound in which two fatty acid groups are attached to sorbitan via an ester bond, and may be selected from among sorbitan dioleate, sorbitan dilinoleate, sorbitan dipalmitoleate, sorbitan dimyristoleate, and a combination thereof.

For use in the present invention, sorbitan unsaturated fatty acid ester is preferably selected from sorbitan monooleate, sorbitan monolinoleate, sorbitan monopalmitoleate, sorbitan monomyristoleate, sorbitan sesquioleate, and a combination thereof.

b) Phospholipid

Phospholipids are essential for the construction of lamellar structures, such as liposomes, in conventional techniques, but cannot form a non-lamellar phase structure, such as a liquid crystal, by themselves. However, phospholipids can participate in the liquid crystal former-driven formation of non-lamellar phase structures, serving to stabilize the resulting liquid crystals.

The phospholipid useful in the present invention is derived from plants or animals, and contains a saturated or unsaturated alkyl ester group of 4 to 30 carbon atoms with a polar head. The phospholipid may be selected from among phosphatidylcholine, phosphatidylethanolamine, phosphatidylserine, phosphatidylglycerine, phosphatidylinositol, phosphatidic acid, sphingomyelin, and a combination thereof according to the structure of the polar head.

Phospholipids are found in plants and animals such as soybeans and eggs. In phospholipids, long alkyl ester groups which account for the hydrophobic tails include saturated fatty acid chains such as mono- and dipalmitoyl, mono- and dimyristoyl, mono- and dilauryl, and mono- and distearyl, and unsaturated fatty acid chains such as mono- or dilinoleyl, mono- and dioleyl, mono- and dipalmitoleyl, and mono- and dimyristoleyl. Saturated and unsaturated fatty acid esters may coexist in phospholipids.

c) Liquid Crystal Hardener

The liquid crystal hardener of the present invention cannot form a non-lamellar structure, unlike the liquid crystal former, nor a lamellar structure such as liposome) unlike phospholipids, by itself. However, the liquid crystal hardener contributes to the liquid crystal former-driven formation of non-lamellar phase structures by increasing the curvature of the non-lamellar structures to enhance the ordered co-existence of oil and water. In the interests of this function, the liquid crystal hardener is advantageously required to have a highly limited polar moiety and a bulky non-polar moiety inside its molecular structure.

In practice, however, biocompatible molecules which are injectable into the body can be selected as the liquid crystal hardener of the present invention only via direct and repeated experiments. As a result, liquid crystal hardeners suitable for the composition of the present invention have molecular structures which are different from one another and thus cannot be elucidated as having only one molecular structure. The common structural feature deduced by observation of all of the liquid crystal hardeners identified is that they are free of ionizable groups, such as carboxyl and amine groups, and have hydrophobic moieties comprising a bulky triacyl group with 15 to 40 carbon atoms or carbon ring structure. Preferred examples of the liquid crystal hardener of the present invention may be free of ionizable groups, such as carboxyl and amine groups, and have at most one hydroxyl and ester group as a weak polar head, with hydrophobic moieties including a bulky triacyl group with 20 to 40 carbon atoms or carbon ring structure. Examples of the liquid crystal hardener of the present invention may include, but are not limited to, triglyceride, retinyl palmitate, tocopherol acetate, cholesterol, benzyl benzoate, ubiquinone, and a combination thereof. Preferably, the liquid crystal hardener may be selected from among tocopherol acetate, cholesterol, and a combination thereof.

d) GnRH Analogues

GnRH analogues are structurally similar to GnRH, but work in different ways in vivo. On the whole, after pulsatile secretion, GnRH performs a biological function to induce the production of sex steroids whereas GnRH analogues are used to potently inhibit the production of sex steroids for a certain period of time in the body.

According to their acting mechanisms, GnRH analogues may be classified into agonists and antagonists. When administered at a therapeutic dose to the body, a GnRH agonist initially binds to a GnRH receptor of the pituitary gland to stimulate the biosynthesis and secretion of follicle stimulating hormone (FSH) and leuteinizing hormone (LH). However, continuation of the administration with the GnRH agonist results in the depletion of the gonadotropin and inhibition of the biosynthesis and secretion of FSH and LH while down-regulating the GnRH receptor. Based on the biological functions of GnRH, GnRH analogues may be applied to the treatment of sex hormone-dependent diseases such as prostate cancer, breast cancer, ovarian cancer, endometriosis, uterine fibroid, polycystic ovary syndrome, hypertrichosis, precocious puberty, gonadotroph pituitary adenomas, sleep apnea syndrome, irritable bowel syndrome, premenstrual syndrome, benign prostatic hyperplasia, and infertility, and may be used as a anticonceptive.

The GnRH agonist as a pharmacologically active substance of the present invention may be selected from among leuprolide, goserelin, triptorelin, nafarelin, buserelin, histrelin, deslorelin, meterelin, gonadrelin, and a pharmaceutically acceptable salt thereof. Preferably, the pharmacologically active substance may be selected from among leuprolide, goserelin and a pharmaceutically acceptable salt thereof.

On the other hand, a GnRH antagonist competes with GnRH for a GnRH receptor of the pituitary gland to block the binding of GnRH to its receptor, thereby suppressing the biosynthesis and secretion of FSH and LH. Examples of the GnRH antagonist as a pharmacologically active substance of the present invention include degarelix, abarelix, ganirelix, cetrorelix, and a pharmaceutically acceptable salt thereof. Preferably, the pharmacologically active substance may be selected from among leuprolide, goserelin and a pharmaceutically acceptable salt thereof.

In the pharmaceutical composition of the present invention, the weight ratio between components of a) and b) suitable for the formation of liquid crystals is in a range of from 10:1 to 1:10, and preferably in a range of 5:1 to 1:5. The weight ratio of a)+b) to c) falls within the range of from 100:1 to 1:1, and preferably within the range of from 50:1 to 2:1. Given these weight ranges, the components efficiently guarantee the sustained release of liquid crystals and the sustained release behaviors can be controlled by regulating the ratio. The suitable weight ratio of a)+b)+c) to d) for providing the sustained release of the GnRH analogue ranges from 10,000:1 to 1:1, and preferably from 1,000:1 to 1:1.

Preferably, the pharmaceutical composition of the present invention comprises a) in an amount of 9~90 weight %; b) in an amount of 9~90 weight %; c) in an amount of 0.1~50 weight %; and d) in an amount of 0.01~50 weight %.

In another embodiment where the pharmacologically active substance is leuprolide, the pharmaceutical composition comprises a) in an amount of 9~64 weight %; b) in an amount of 18~76 weight %; c) in an amount of 1~36 weight %; and d) leuprolide, or a pharmaceutically acceptable salt thereof in an amount of 0.1~50 weight % but are not limited thereto.

In another embodiment where the pharmacologically active substance is goserelin, the pharmaceutical composition comprises a) in an amount of 9~64 weight %; b) in an amount of 18~76 weight %; c) in an amount of 1~36 weight %; and d) goserelin or a pharmaceutically acceptable salt thereof in an amount of 0.1~50 weight % but are not limited thereto.

In a further embodiment where the pharmacologically active substance is degarelix, the pharmaceutical composition comprises a) in an amount of 9~64 weight %; b) in an amount of 18~76 weight %; c) in an amount of 1~36 weight %; and d) degarelix or a pharmaceutically acceptable salt thereof in an amount of 2~50 weight % but are not limited thereto.

Given the content ranges of components a) to d), the pharmaceutical compositions of the present invention exhibit excellent sustained release behavior.

As used herein, the term "aqueous fluid" is intended to include water and body fluid such as a mucosal solution, a tear, a sweat, a saliva, a gastrointestinal fluid, an extravascular fluid, an extracellular fluid, an interstitial fluid, and a blood plasma. When brought into body surfaces, regions or cavities (e.g. inside the body) whose external environments are formed for by aqueous fluids, the pharmaceutical composition of the present invention undergoes transition from a liquid phase to a liquid crystalline phase with a semi-solid appearance. That is, the pharmaceutical composition of the present invention exists as a liquid state before application to the human body and shifts into a liquid crystalline phase with sustained release behavior within the body.

The liquid crystals formed by the pharmaceutical composition of the present invention have a non-lamellar phase structure in which oil and water are in an ordered mixture and arrangement without distinction between inner and out phases. The ordered arrangement of oil and water renders the non-lamellar phase structure of a mesophase, which is a state of matter intermediate between liquid and solid.

The pharmaceutical composition of the present invention is different from conventional compositions that are lamellar structures, such as micelles, emulsions, microemulsions, liposomes, and lipid bilayers, which have been widely used in designing pharmaceutical formulations. Such lamellar structures are in oil in water (o/w) or water in oil (w/o) type in which there have an arrangement with inner and out phases.

The term "liquid crystallization," as used herein, refers to the formation of liquid crystals having a non-lamellar phase structure from the pre-concentrate upon exposure to aqueous fluid.

The pharmaceutical composition of the present invention may be prepared at room temperature from a) at least one liquid crystal former, b) at least one phospholipid, c) at least one liquid crystal hardener, and d) at least one GnRH analogue, and if necessary, by heating or using a homogenizer. The homogenizer may be a high-pressure homogenizer, an ultrasonic homogenizer, a bead mill homogenizer, and etc.

As described above, the sustained-release lipid pre-concentrate of the present invention may be a pharmaceutical composition which exists in a liquid phase in the absence of aqueous fluid and forms into liquid crystals in the presence of aqueous fluid. As it turns to a pharmaceutical composition which can be applied to the body using a method selected from among injection, coating, dripping, padding, oral administration, and spraying, the pre-concentrate of the present invention may be preferably formulated into various dosage forms including injections, ointments, gels, lotions, capsules, tablets, solutions, suspensions, sprays, inhalants, eye drops, adhesives, plaster and pressure sensitive adhesives.

Particularly, when an injection route is taken, the pharmaceutical composition of the present invention may be administered by subcutaneous or intramuscular injection or other injection routes depending on the properties of the pharmacologically active substance.

The pharmaceutical composition of the present invention may be preferably in the formulation form selected from among injections, ointments, gels, lotions, capsules, tablets, solutions, suspensions, sprays, inhalants, eye drops, adhesives, plaster and pressure sensitive adhesives, and more preferably into injections.

The pharmaceutical composition of the present invention may be prepared by adding a pharmacologically active substance to the pre-concentrate of the present invention. As needed, heat or a homogenizer may be used in the preparation of the pharmaceutical composition of the present invention, but this is not a limiting factor to the present invention.

The dose of the pharmaceutical composition of the present invention adheres to the well-known dose of the pharmacologically active substance employed, and may vary depending on various factors including the patient's condition, age and sex. It may be administered orally or parenterally depending on the properties of the pharmacologically active substance.

In accordance with a further aspect thereof, the present invention contemplates a method of maintaining pharmaceutical efficacy through the sustained release of a pharmacologically active substance by administering the pharmaceutical composition of the present invention to a mammal including a human, and the use of the pharmaceutical composition for the sustained release of a pharmacologically active substance.

Advantageous Effects of Invention

As described hitherto, the pharmaceutical composition of the present invention, based on a sorbitan unsaturated fatty acid ester, is highly safe and exists in a liquid phase in the absence of aqueous fluid but rapidly changes into liquid crystals upon exposure to aqueous fluid within the body. Therefore, the pharmaceutical composition can be easily administered, exhibits excellent sustained release of a GnRH analogue without side effects such as pain and inflammation, compared to conventional sustained release formulations in solid particle phases.

BRIEF DESCRIPTION OF DRAWINGS

FIG. 1 illustrates phase change behaviors of compositions of Examples 2, 6, 9 and 12 upon exposure to aqueous fluid.

FIG. 2 shows the liquid crystalline structures of the compositions of Examples 2 and 6, formed in aqueous fluid.

FIG. 3 shows the in vivo drug release behaviors of the compositions of Example 2 and Comparative Example 1.

FIG. 4 shows the in vivo drug release behaviors of the compositions of Example 6 and Comparative Example 2.

MODE FOR THE INVENTION

The following non-limiting Examples serve to illustrate selected embodiments of the invention. It will be appreciated that variations in proportions and alternatives in elements of the components shown will be apparent to those skilled in the art and are within the scope of embodiments of the present invention.

The additives and excipients used in the present invention satisfied the requirements of the Pharmacopoeia and were purchased from Aldrich, Lipoid, Croda, and Seppic.

[Examples 1 to 12] Preparation of Pharmaceutical Compositions

Sorbitan unsaturated fatty acid esters, phospholipids, liquid crystal hardeners, and pharmacologically active substances were added, at the weight ratios given in Table 1, below.

In Examples 1 to 12, the substances were homogeneously mixed in a water bath maintained at 20~75° C. using a homogenizer (PowerGen model 125. Fisher) for 0.5~3 hrs at 1000~3000 rpm. The resulting lipid solutions were left at room temperature to come to thermal equilibrium at 25° C., followed by adding each of the pharmacologically active substances leuprolide acetate, goserelin acetate, and degarelix acetate thereto. Then, the substances were homogenized using a homogenizer for about 5~30 mins at 1,000~3,000 rpm to prepare pharmaceutical compositions in a liquid phase.

TABLE 1

| (Unit: mg) | 1 | 2 | 3 | 4 | 5 | 6 | 7 | 8 | 9 | 10 | 11 | 12 |
|---|---|---|---|---|---|---|---|---|---|---|---|---|
| | | | | | | Example | | | | | | |
| Leuprolide acetate | 3.75 | 3.75 | 3.75 | 3.75 | 11.25 | 11.25 | 22.5 | 22.5 | | | | |
| Goserelin acetate | | | | | | | | | 3.78 | 3.78 | | |
| Degarelix acetate | | | | | | | | | | | 80 | 80 |
| Sorbitan monooleate | | 32 | | 35 | | 75 | | 150 | 36 | | 51.0 | 25 |
| Sorbitan sesquioleate | 43.4 | | 45.8 | | 68 | | 120 | | | 35.0 | | |
| Phosphatidyl choline | | 40 | | 45 | 95 | 101.3 | 156 | 202.6 | 40 | 50 | | 35 |
| Phosphatidyl ethanolamine | 36.6 | | 40.7 | | | | 10 | | | | 38.2 | |
| Tocopherol acetate | 6 | 9 | | 15 | 45 | 30 | 65 | 60 | 15 | 10.0 | 5.8 | 12 |
| Cholesterol | 10 | 4 | 13.5 | | 15 | 11.3 | 22 | 22.6 | 4 | | | 4 |
| Ubiquinone | 4 | | | | | | | | | 5 | | |
| DMSO | | 5 | | | | 15 | | 5 | 5 | | | |
| Ethanol | | 10 | | 5 | | 28.1 | 30 | | | | | 10 |
| Form in aqueous phase | | | | | | Liquid Crystal | | | | | | |

Comparative Examples 1 and 2

For the formulation of Comparative Example 1, Leuplin DPS(CJ) containing leuprolide acetate as a pharmacologically active substance was used in an amount of 3.75 mg.

As the formulation of Comparative Example 2, 11.25 mg of Leuplin DPS(CJ) containing the pharmacologically active substance leuprolide acetate was used.

[Experimental Example 1] Contents of Pharmacologically Active Substances in Pharmaceutical Compositions To examine whether the pharmaceutical compositions prepared in Examples contained pharmacologically active substances at a therapeutically effective concentration, the contents of leuprolide acetate were quantitated by HPLC, as follows.

Each of the pharmaceutical compositions was dissolved in an amount corresponding to 2.5 mg of leuprolide acetate in a mobile phase (triethylamine buffer:acetonitrile:n-propyl alcohol=85:9:6), and centrifuged for 10 min at 1500 rpm, followed by filtering the supernatants of the test sample through a 0.2 μm filter. For comparison, a standard sample with the same concentration as that of the test samples was prepared from a leuprolide acetate standard. The standard sample and the test samples were loaded in an injection volume of 20 μL at a flow rate of 1.0~1.5 mL/min to 4.6×100 mm, 3 μm packing L1 column or like, and quantitatively analyzed at 220 nm using a UV spectrometer. Average contents of leuprolide acetate in the pharmaceutical compositions were obtained from three measurements (see Table 2).

TABLE 2

| | Example | | | | | | | |
|---|---|---|---|---|---|---|---|---|
| (Unit: %) | 1 | 2 | 3 | 4 | 5 | 6 | 7 | 8 |
| Content | 100.3 | 101.2 | 99.8 | 98.9 | 102.9 | 99.4 | 100.5 | 99.1 |

As can be seen in Table 2, all of the pharmaceutical compositions prepared in Examples 1 to 8 ideally contained leuprolide acetate in amounts within standard content (100%)±3%.

[Experimental Example 2] Formation of Liquid Crystals in Aqueous Fluid

An examination was made to confirm whether the pharmaceutical compositions prepared in Examples form ideal liquid crystals in aqueous fluid. In this regard, the compositions of Examples 2, 6, 9, and 12 which were in liquid phase were loaded into syringes and then injected to 2 g of PBS (pH 7.4). The results are depicted in FIG. 1.

The pharmaceutical compositions prepared in Examples 1 to 12 existed in liquid phase in the absence of aqueous fluid. When injected into an aqueous fluid (PBS), the pharmaceutical compositions in liquid phase forms into spherical liquid crystals, indicating that the pharmacologically active substance GnRH analogue has no influence on the formation of the pharmaceutical compositions into liquid crystals.

[Experimental Example 3] Structural Determination of Liquid Crystals in Aqueous Fluid The liquid crystals of the pharmaceutical compositions of Examples 2 and 6, formed in aqueous fluid, were observed for structure under a polarization microscope (Motic, BA 300 Pol) (FIG. 2).

A slide glass was very thinly coated with each of the pharmaceutical compositions of Examples 2 and 6, and left for 4 hrs in deionized water in a schale to form liquid crystals. After being covered with a cover glass to prevent the introduction of air, the test sample on slide glass was observed at 200× magnification using a polarization microscope (Motic, BA 300 Pol). As can be seen in FIG. 2, the pharmaceutical compositions of Examples 2 and 6 are formed into liquid crystals with typical hexagonal crystalline structures for excellent sustained release.

When an account is taken of results from Experimental Examples 1 to 3, the pharmaceutical compositions of the present invention can form physiochemically stable, ideal liquid crystals in the presence of aqueous fluid even if they contain pharmacologically active substances which have large molecular weights and relatively high hydrophobicity.

[Experimental Example 4] In Vivo PK Profile of Pharmaceutical Compositions

Drug release behaviors from the pharmaceutical compositions of the present invention were examined in vivo in the following test.

Using a disposable syringe, each of the pharmaceutical compositions of Examples 2 and 6 was subcutaneously injected at a leuprolide acetate dose of 12.5 mg/kg (corresponding to a 28-day dose for humans) into the back of 6 SD rats (male), 9 weeks old, with an average body weight of 300 g. For comparison with PK profiles of PLGA microparticle formulations, the pharmaceutical compositions of Comparative Examples 1 and 2 were subcutaneously injected at a leuprolide acetate dose of 12.5 mg/kg (corresponding to a 28-day dose for humans) into the back of 6 SD rats (male), 9 weeks old, with an average body weight of 300 g.

Leuprolide acetate concentrations in plasma samples taken from the SD rats were monitored for 28 days using LC-MS/MS (liquid chromatography-mass spectrometry) to draw PK profiles (pharmacokinetic profiles). The average of leuprolide acetate concentration taken from the 6 SD rats are plotted in graph of each of FIGS. 3 and 4, and expressed as calculated logarithm values in the lower graph of each of FIGS. 3 and 4 to examine a difference in drug concentration of rat plasma at the late phase.

The PK profiles in SD rats of the pharmaceutical compositions of Comparative Example 1 and Example 2 are shown in FIG. 3. As a control (reference drug) for Example 2, Comparative Example 1 was of 3.75 mg of Leuplin DPS(CJ), which is widely used as a 1-month formulation of leuprolide acetate. Compared to the control (reference drug) of Comparative Example 1, the pharmaceutical composition of Example 2 exhibited ideal pK behavior and excellent sustained release. The pharmaceutical composition of Example 2 had an initial burst concentration of 81 ng/mL, which is about half reduced, compared to 155 ng/mL of Comparative Example 1, thus achieving an exceptional improvement in initial burst concentration, a typical problem with PLGA microparticle formulations. In contrast to the composition of Comparative Example 1 which became unstable in PK behavior from 5 days after administration, the pharmaceutical composition of Example 2 maintained very stable effective plasma concentration of leuprolide acetate.

FIG. 4 shows the PK profiles in SD rats of the pharmaceutical compositions of Comparative Example 2 and Example 6. As a control (reference drug) for Example 6, Comparative Example 2 was of 11.25 mg of Leuplin DPS (CJ), which is widely used as a 3-month formulation of leuprolide acetate. Compared to the control (reference drug) of Comparative Example 2, the pharmaceutical composition of Example 6 exhibited ideal pK behavior required for sustained release formulations, and particularly excellent sustained release for a long-term. The composition of Comparative Example 2 showed an initial burst concentration about three times as high as that of Comparative Example 1, which was believed to be attributed to the difference of drug content therebetween. Although the pharmaceutical composition of Example 6 was 3-fold higher in drug content than that of Example 2, no observations were made of the rapid increase in initial burst concentration, unlike the composition of Comparative Example 2. The initial burst concentration was measured to be 114 ng/ml, which is about 4-fold smaller than 484 ng/ml, which was measured at the initial phase in the composition of Comparative Example 2. In addition, the composition of Comparative Example 2 had blood leuprolide acetate levels from 10 days after administration, which was significantly lower level compared to the composition of Comparative Example 1 in the mid- to later phase, drawing an unstable PK profile. On the other hand, the pharmaceutical composition of Example 6 allowed for a blood leuprolide acetate level curve which was similar to that of Example 2 in the mid- to late phase, demonstrating that the pharmaceutical composition of the present invention, even though 3-fold increasing in drug content, maintained excellent long-term sustained release.

The invention claimed is:

1. A pharmaceutical composition, comprising:
   a) at least one sorbitan unsaturated fatty acid ester having a polar head with at least two or more —OH (hydroxyl) groups;
   b) at least one phospholipid;
   c) at least one liquid crystal hardener, which is free of an ionizable group, having a hydrophobic moiety of 15 to 40 carbon atoms with a triacyl group or a carbon ring structure; and
   d) at least one GnRH (gonadotropin-releasing hormone) analogue as a pharmacologically active substance,
   wherein the pharmaceutical composition exists as a liquid phase in the absence of aqueous fluid and forms into a liquid crystal in the presence of aqueous fluid.

2. The pharmaceutical composition of claim 1, wherein the sorbitan unsaturated fatty acid ester is selected from the group consisting of sorbitan monooleate, sorbitan monolinoleate, sorbitan monopalmitoleate, sorbitan monomyristoleate, sorbitan sesquioleate, sorbitan sesquilinoleate, sorbitan sesquipalmitoleate, sorbitan sesquimyristoleate, sorbitan dioleate, sorbitan dilinoleate, sorbitan dipalmitoleate, sorbitan dimyristoleate, and a combination thereof.

3. The pharmaceutical composition of claim 1, wherein the sorbitan unsaturated fatty acid ester is selected from the group consisting of sorbitan monooleate, sorbitan monolinoleate, sorbitan monopalmitoleate, sorbitan monomyristoleate, sorbitan sesquioleate, and a combination thereof.

4. The pharmaceutical composition of claim 1, wherein the phospholipid contains a saturated or unsaturated alkyl ester group of 4 to 30 carbon atoms and is selected from the group consisting of phosphatidylcholine, phosphatidylethanolamine, phosphatidylserine, phosphatidylglycerine, phosphatidylinositol, phosphatidic acid, sphingomyelin, and a combination thereof.

5. The pharmaceutical composition of claim 4, wherein the phospholipid is phosphatidylcholine.

6. The pharmaceutical composition of claim 1, wherein the liquid crystal hardener is selected from the group consisting of triglyceride, retinyl palmitate, tocopherol acetate, cholesterol, benzyl benzoate, ubiquinone, and a combination thereof.

7. The pharmaceutical composition of claim 1, wherein the liquid crystal hardener is tocopherol acetate, cholesterol, and a combination thereof.

8. The pharmaceutical composition of claim 1, wherein the GnRH analogue is a GnRH agonist or a GnRH antagonist.

9. The pharmaceutical composition of claim 8, wherein the GnRH agonist is selected from the group consisting of leuprolide, goserelin, triptorelin, nafarelin, buserelin, histrelin, deslorelin, meterelin, gonadorelin, a pharmaceutically acceptable salt thereof, and a combination thereof.

10. The pharmaceutical composition of claim 8, wherein the GnRH antagonist is selected from the group consisting of degarelix, abarelix, ganirelix, cetrorelix, a pharmaceutically acceptable salt thereof, and a combination thereof.

11. The pharmaceutical composition of claim 1, wherein the GnRH analogue is selected from the group consisting of leuprolide, goserelin, triptorelin, degarelix, abarelix, a pharmaceutically acceptable salt thereof, and a combination thereof.

12. The pharmaceutical composition of claim 1, wherein the GnRH analogue is leuprolide or a pharmaceutically acceptable salt thereof.

13. A method for treating a sex hormone-dependent disease, comprising administering a pharmaceutical composition of claim 1 to a subject in need thereof.

14. The method of claim 13, wherein the sex hormone-dependent disease is selected from the group consisting of prostate cancer, breast cancer, ovarian cancer, endometriosis, uterine fibroid, polycystic ovarian disease, precocious puberty, hypertrichosis, gonadotroph pituitary adenomas, sleep apnea syndrome, irritable bowel syndrome, premenstrual syndrome, benign prostatic hyperplasia, and infertility.

15. The pharmaceutical composition of claim 1, wherein a weight ratio of a) to b) ranges from 10:1 to 1:10.

16. The pharmaceutical composition of claim 1, wherein a weight ratio of a)+b) to c) ranges from 1,000:1 to 1:1.

17. The pharmaceutical composition of claim 1, wherein a weight ratio of a)+b)+c) to d) ranges from 10,000:1 to 1:1.

18. The pharmaceutical composition of claim 1, comprising:
   a) at least one sorbitan unsaturated fatty acid ester having a polar head with at least two or more —OH (hydroxyl) groups in an amount of 9-90 weight %;
   b) at least one phospholipid in an amount of 9-90 weight %;
   c) at least one liquid crystal hardener which is free of an ionizable group and has a triacyl group with 15 to 40 carbon atoms or a carbon ring structure in a hydrophobic moiety in an amount of 0.1-50 weight %; and
   d) at least one GnRH (gonadotropin-releasing hormone) analogue in an amount of 0.01-50 weight %.

19. The pharmaceutical composition of claim 1, comprising:
   a) at least one sorbitan unsaturated fatty acid ester having a polar head with at least two or more —OH (hydroxyl) groups in an amount of 9-64 weight %;
   b) at least one phospholipid in an amount of 18-76 weight %;
   c) at least one liquid crystal hardener which is free of an ionizable group and has a triacyl group with 15 to 40 carbon atoms or a carbon ring structure in a hydrophobic moiety in an amount of 1-36 weight %; and
   d) leuprolide or a pharmaceutically acceptable salt thereof in an amount of 0.1-50 weight %.

20. The pharmaceutical composition of claim 1, comprising:
   a) at least one sorbitan unsaturated fatty acid ester having a polar head with at least two or more —OH (hydroxyl) groups in an amount of 9-64 weight %;
   b) at least one phospholipid in an amount of 18-76 weight %;
   c) at least one liquid crystal hardener which is free of an ionizable group and has a triacyl group with 15 to 40 carbon atoms or a carbon ring structure in a hydrophobic moiety in an amount of 1-36 weight %; and
   d) goserelin or a pharmaceutically acceptable salt thereof in an amount of 0.1-50 weight %.

21. The pharmaceutical composition of claim 1, comprising:
   a) at least one sorbitan unsaturated fatty acid ester having a polar head with at least two or more —OH (hydroxyl) groups in an amount of 9-64 weight %;
   b) at least one phospholipid in an amount of 18-76 weight %;
   c) at least one liquid crystal hardener which is free of an ionizable group and has a triacyl group with 15 to 40 carbon atoms or a carbon ring structure in a hydrophobic moiety in an amount of 1-36 weight %; and
   d) degarelix or a pharmaceutically acceptable salt thereof in an amount of 2-50 weight %.

22. The pharmaceutical composition of claim 1, being in a formulation, said formulation being selected from the group consisting of an injection, an ointment, a gel, a lotion, a capsule, a tablet, a solution, a suspension, a spray, an inhalant, an eye drop, an adhesive, a plaster, and a pressure sensitive adhesive.

23. The pharmaceutical composition of claim 22, wherein the formulation is an injection.

24. A contraceptive, comprising the pharmaceutical composition of claim 1.

* * * * *